US011285114B2

(12) United States Patent
Singh et al.

(10) Patent No.: US 11,285,114 B2
(45) Date of Patent: Mar. 29, 2022

(54) CORE-SHELL COMPOSITE MATERIAL

(71) Applicants: AGENCY FOR SCIENCE, TECHNOLOGY AND RESEARCH, Singapore (SG); MASSEY UNIVERSITY, Palmerston North (NZ); AGRESEARCH, Hamilton (NZ)

(72) Inventors: Harjinder Singh, Palmerston North (NZ); Brendan Haigh, Hamilton (NZ); Nicole Roy, Palmerston North (NZ); Maxim Kiryukhin, Singapore (SG); Maria Antipina, Singapore (SG); Marina Novoselova, Singapore (SG); Gleb Sukhorukov, London (GB)

(73) Assignees: AGENCY FOR SCIENCE, TECHNOLOGY AND RESEARCH, Singapore (SG); MASSEY UNIVERSITY, Palmerston North (NZ); AGRESEARCH, Hamilton (NZ)

( * ) Notice: Subject to any disclaimer, the term of this patent is extended or adjusted under 35 U.S.C. 154(b) by 0 days.

(21) Appl. No.: 15/771,399

(22) PCT Filed: Oct. 26, 2016

(86) PCT No.: PCT/SG2016/050525
§ 371 (c)(1),
(2) Date: Apr. 26, 2018

(87) PCT Pub. No.: WO2017/074262
PCT Pub. Date: May 4, 2017

(65) Prior Publication Data
US 2018/0344650 A1 Dec. 6, 2018

(30) Foreign Application Priority Data
Oct. 26, 2015 (SG) .............................. 10201508831S

(51) Int. Cl.
*A61K 9/48* (2006.01)
*A61K 47/38* (2006.01)
*A61K 47/42* (2017.01)
*A61K 47/44* (2017.01)
*A61K 9/50* (2006.01)
*A61K 47/34* (2017.01)
*A61K 9/19* (2006.01)

(52) U.S. Cl.
CPC .......... *A61K 9/4825* (2013.01); *A61K 9/4833* (2013.01); *A61K 9/4891* (2013.01); *A61K 9/5073* (2013.01); *A61K 47/34* (2013.01); *A61K 47/38* (2013.01); *A61K 47/42* (2013.01); *A61K 9/19* (2013.01)

(58) Field of Classification Search
None
See application file for complete search history.

(56) References Cited

U.S. PATENT DOCUMENTS

| 2001/0008638 A1 | 7/2001 | Wilding |
| 2008/0176080 A1 | 7/2008 | Haynie |
| 2009/0061006 A1 | 3/2009 | Leuschner et al. |
| 2011/0305754 A1 | 12/2011 | Mishra et al. |

FOREIGN PATENT DOCUMENTS

CN  1399544 A  2/2003

OTHER PUBLICATIONS

Shutava et al. (J Nanosci. Nanotechnol. 2006, vol. 6, No. 6).*
Lomova et al., "Multilayer Capsules of Bovine Serum Albumin and Tannic Acid for Controlled Release by Enzymatic Degradation," ACS Applied Materials & Interfaces, 7(22): 11732-11740, May 19, 2015.
Sadovoy et al., "Layer-by-Layer Assembled Multilayer Shells for Encapsulation and Release of Fragrance," ACS Applied Materials & Interfaces, 5(18): 8948-8954, Aug. 14, 2013.
Shutava et al., "(−)-Epigallocatechin gallate/gelatin layer-by-layer assembled films and microcapsules," Journal of Colloid and Interface Science, 330(2): 276-283, Nov. 7, 2008.
De Geest et al., "Release Mechanisms for polyelectrolyte capsules," Chemical Society Reviews, 36(4): 636-649, Oct. 13, 2006.
Notification of the Transmittal of the International Search Report and the Written Opinion of the International Searching Authority, or the the Declaration for International Application No. PCT/SG2016/050525 dated Jan. 10, 2017.
Notification of Transmittal of International Preliminary Report on Patentability for International Application No. PCT/SG2016/050525 dated Oct. 24, 2017.
Novoselova, et al., "Materials Selection for Production of Microspheres Protecting Lactoferrin Under Acid Conditions", Science Evolution, vol. 1, Jun. 30, 2016, pp. 92-102.
H.H. Lau, et al., "Protein-tannic Acid Multilayer Films: A Multifunctional Material for Microencapsulation of Food-Derived Bioactives", Journal of Colloid and Interface Science, Nov. 1, 2017, vol. 505, pp. 332-340.
Notice of Reasons for Refusal of the Japanese Patent Office dated Aug. 18, 2020 for related Japanese Application No. 2018-542106.
Notice of Reasons for Refusal of the Japanese Patent Office dated Jan. 12, 2021 for related Japanese Application No. 2018-542106.

* cited by examiner

*Primary Examiner* — Patricia Duffy
*Assistant Examiner* — Garen Gotfredson
(74) *Attorney, Agent, or Firm* — Womble Bond Dickinson (US) LLP

(57) ABSTRACT

Disclosed herein is a core-shell composite material comprising: a core optionally comprising an active ingredient compound; a shell structure comprising at least two alternating layers; the alternating layers being a protein layer and a polyphenol layer; and optionally a polyelectrolyte layer interfacing said core and said shell structure, said polyelectrolyte layer being disposed adjacent to said protein layer or said polyphenol layer, wherein said shell structure is selected to be resistant to degradation under gastric conditions but is degradable by one or more intestinal enzymes. In a preferred embodiment the protein is bovine serum albumin (BSA) or pepsin, the polyphenol layer is tannin or tannic acid, and the shell structure is degradable by pepsin.

13 Claims, 8 Drawing Sheets

[Figure 1]
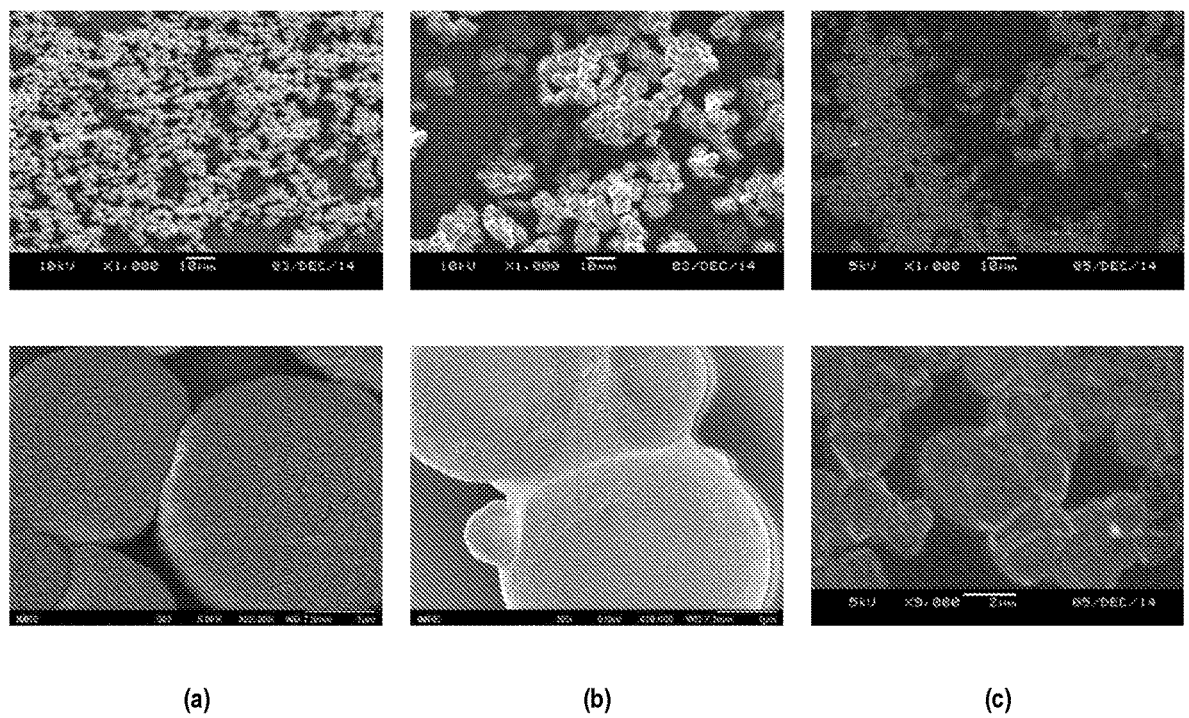
(a)                  (b)                  (c)

[Figure 2]
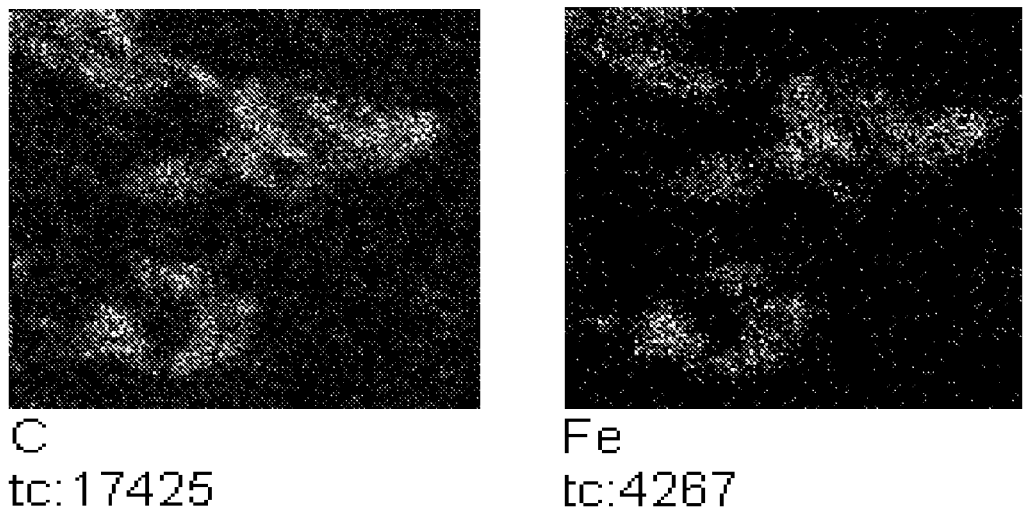
(a)
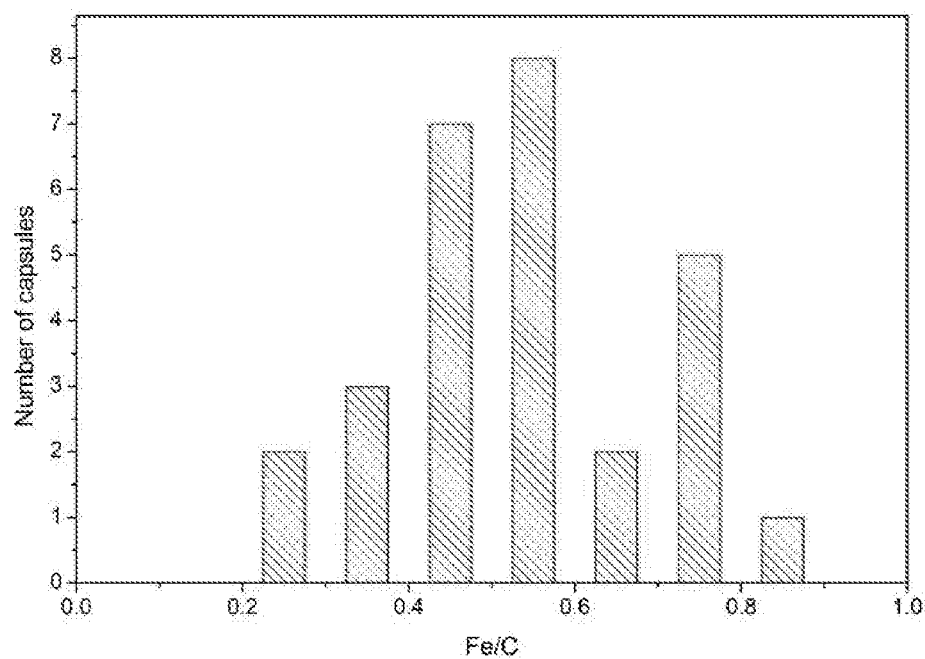
(b)

[Figure 3]
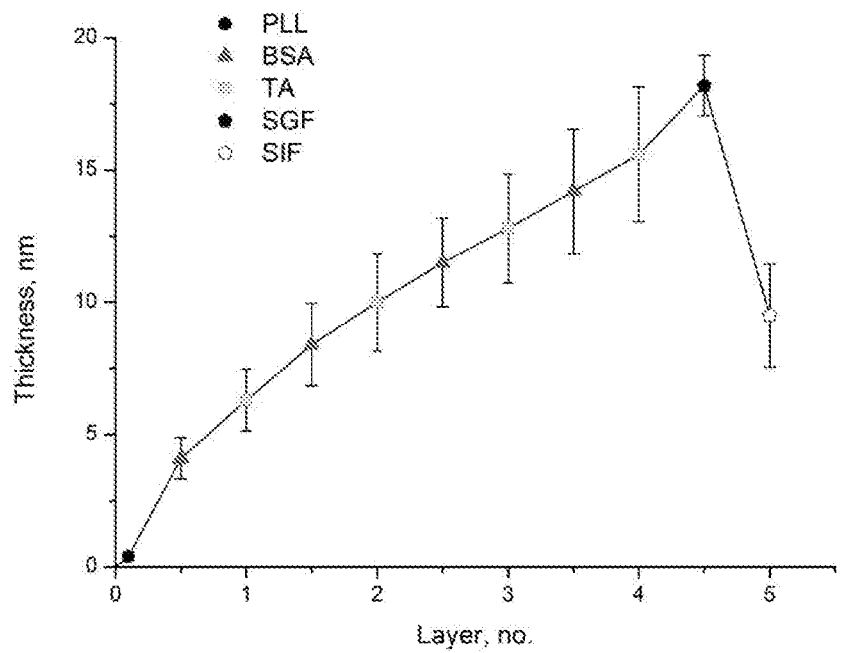
(a)
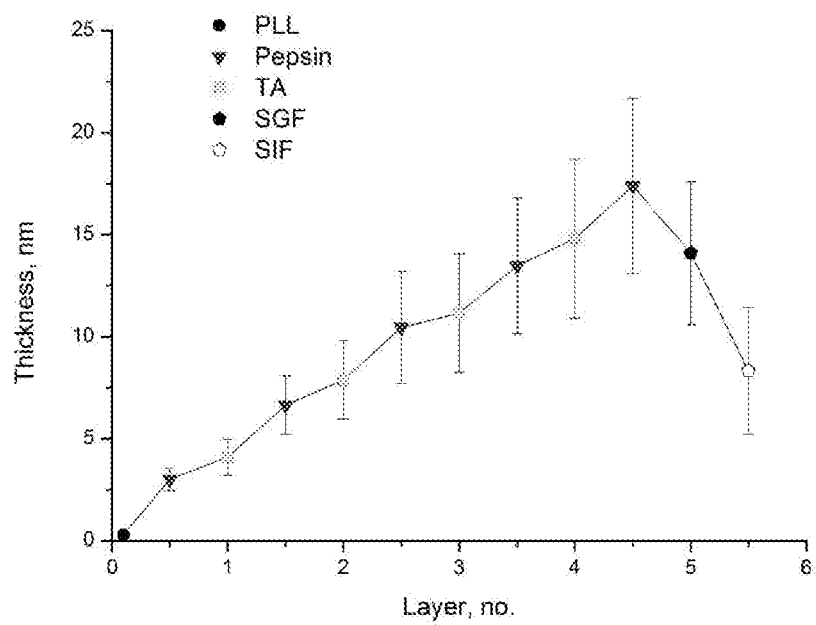
(b)

[Figure 4]
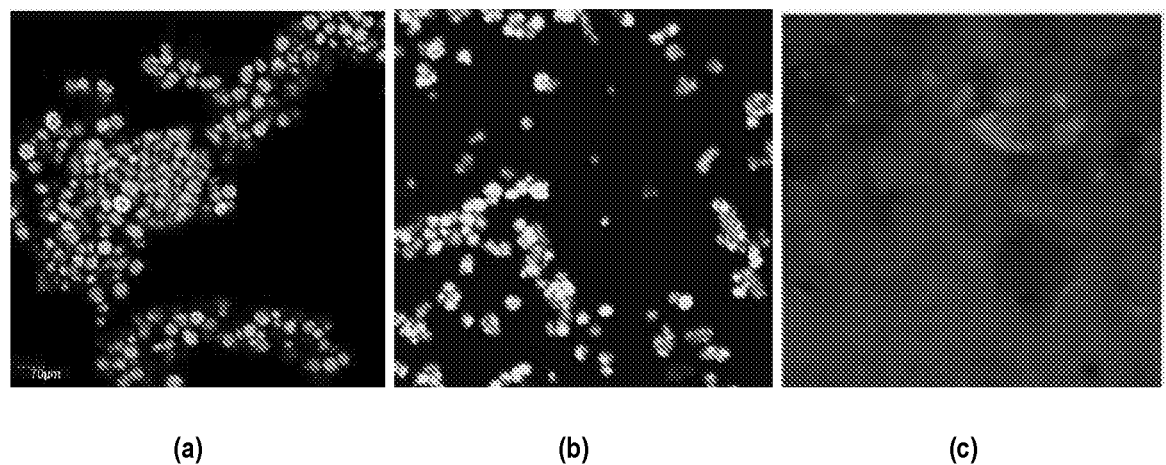
(a)  (b)  (c)

[Figure 5]
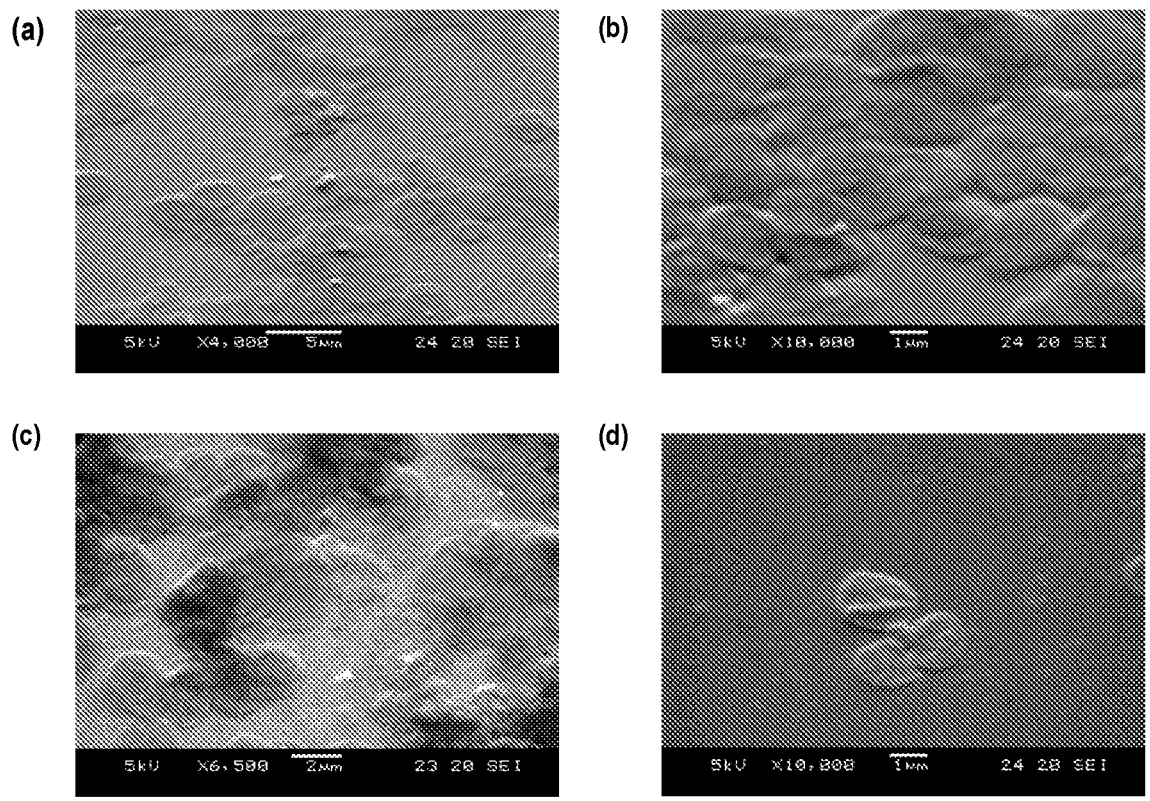

[Figure 6]
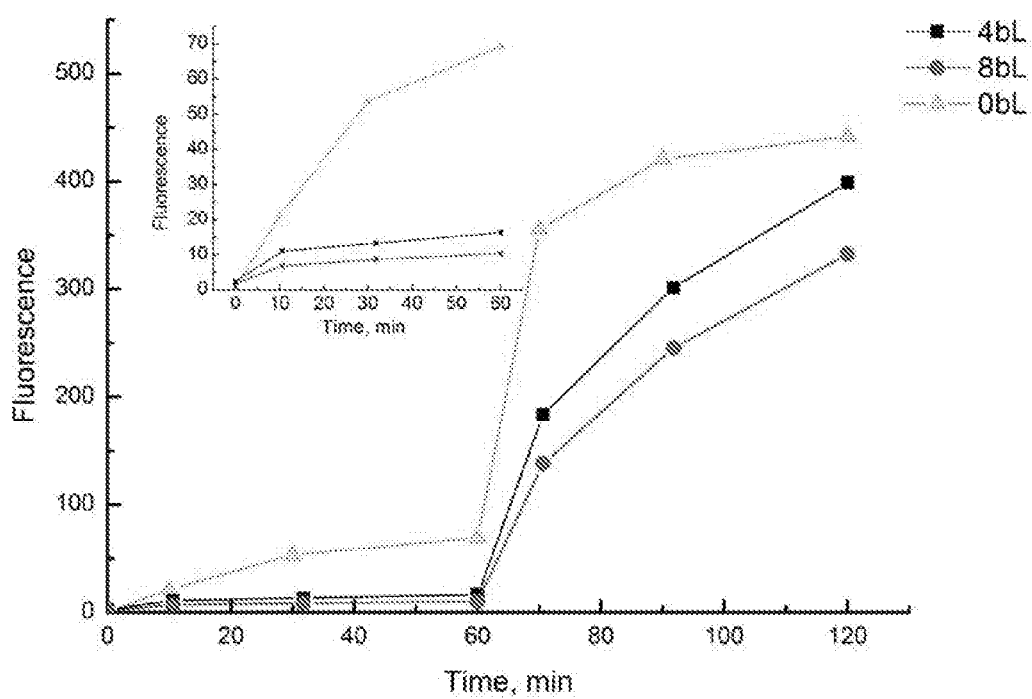

[Figure 7]
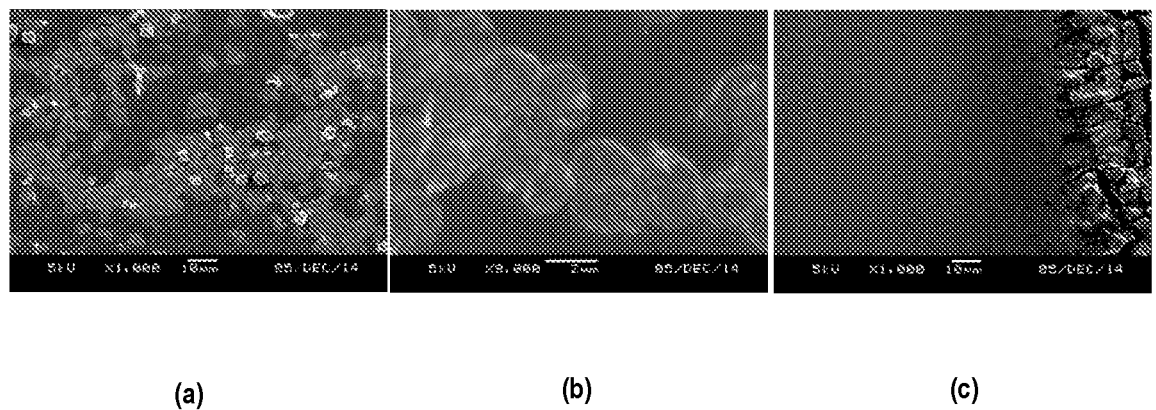
(a) (b) (c)

[Figure 8]
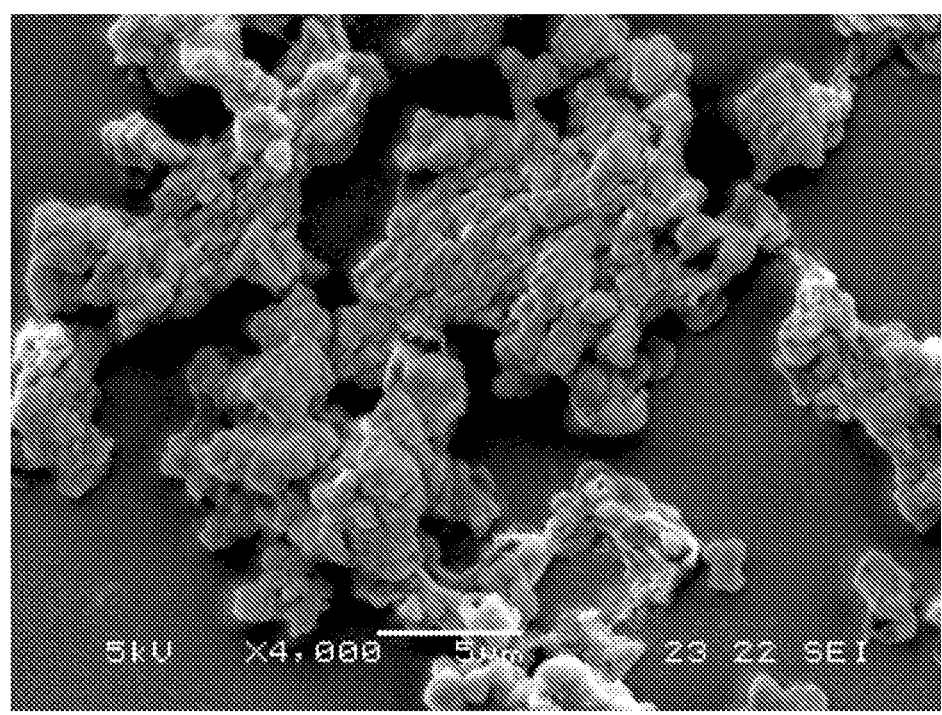

CORE-SHELL COMPOSITE MATERIAL

CROSS-REFERENCE TO RELATED APPLICATIONS

This present application is a U.S. National Phase application under 35 U.S.C. § 371 of International Application No. PCT/SG2016/050525, filed 26 Oct. 2016, entitled CORE-SHELL COMPOSITE MATERIAL, which claims priority to Singapore patent application no. 10201508831S filed on 26 Oct. 2015.

TECHNICAL FIELD

The present invention generally relates to a core-shell composite material for targeted delivery of a compound or an active ingredient.

BACKGROUND ART

The targeted delivery of compounds, e.g., bioactives, active ingredients, drugs, vitamins, proteins, hormones, enzymes, etc., to desired absorption sites in the human or animal body is an ever-present technical issue for both nutrition-based and pharmaceutical industries.

The compounds to be transported often exhibit limited bioavailability due to their poor solubility in aqueous medium and instability in the gastric fluid. These compounds may be sensitive to pH and may experience enzymatic degradation in the gastric fluid. Absorption of nutrients by the human body takes place mainly in the small intestine. As such, these compounds may be substantially degraded before they even reach the small intestine.

In order to reap maximum health benefits, such compounds have to be protected from degradation in the gastric fluid. Traditionally, gelatin capsules have been used in food formulations for delayed release of food ingredients. Even though gelatin is safe, readily available and can be obtained at relatively low cost, it is soluble in the acidic environment of the gastric fluid. Hence, gelatin capsules may not be suitable for transporting compounds intended for delivery to the small intestine.

In order to overcome the problem of premature release of the transported compounds in the gastric fluid, multilayer capsules have been proposed to prevent degradation of the capsule in the gastric fluid. Currently, the controlled release of compounds using such multilayer capsules is dependent on changes in pH. For example, a multilayer capsule encapsulating a bioactive compound may remain intact at low pH of the gastric fluid but may structurally deform at higher pH of the intestinal fluid, resulting in the release of the encapsulated compound. It is therefore necessary to store such encapsulated product under acidic conditions prior to consumption which may affect the palatability of the food product and the stability of the other components found in the food product. Furthermore, where the compounds to be transported are adsorbed onto solid supports or mixed with pharmaceutically acceptable carriers, such supports or carriers may risk decomposition by the gastric fluids. As a result, premature release of the compounds or contamination of the transported compounds may occur.

Additionally, for compound delivery mechanisms that are triggered by changes in pH conditions, there is a need to account for variation of the pH profile in the gastrointestinal tract (GIT) of each individual person or animal, which may be caused by differences in diet, stomach fill, genetics, and/or gastrointestinal disorders. Such variations pose difficulty in designing a comprehensive delivery system suitable for use in general.

Hence, there is a need to provide a material that can be used for transporting a compound for targeted delivery, preferably to the small intestine.

SUMMARY OF INVENTION

According to a first aspect, there is provided a core-shell composite material comprising: a) a core optionally comprising an active ingredient compound; b) a shell structure comprising at least two alternating layers; the alternating layers being selected from a protein layer or a polyphenol layer; and optionally c) a polyelectrolyte layer interfacing said core and said shell structure, said polyelectrolyte layer being disposed adjacent to said protein layer or said polyphenol layer, wherein said shell structure is selected to be resistant to degradation under gastric conditions but is degradable by one or more intestinal enzymes.

The disclosed composite material is capable of withstanding degradation under gastric conditions. Gastric conditions may refer to a simulated acidic mixture containing one or more naturally-occurring or synthetic enzymes released by stomach chief cells, or physiological/biological gastric conditions. The shell structure of the disclosed composite material may comprise one or more protein layers interposed between polyphenol layers. The protein layers may be same or different and are independently provided. The polyphenol layers may be same or different and are independently provided.

The protein layer may be one that is substantially resistant to degradation or hydrolysis by stomach enzymes, e.g., pepsin, or gastric lipase. Advantageously, this property allows the core-shell composite material to pass through the stomach of a human/animal subject without substantially releasing (or with minimal release of) its contents, e.g., the active ingredient core encapsulated therein. Advantageously, the disclosed composite provides targeted delivery of the active ingredient to a desired location of the body, e.g., the small intestine. Advantageously, the disclosed composite may be composed of readily available proteins, which implies cost-effectiveness for the manufacture of the core-shell composite. Further advantageously, the disclosed composite may be synthesized via a straightforward layer by layer deposition process.

According to another aspect, there is provided a method of preparing a core-shell composite material as disclosed above, the method comprising the steps of: a) alternately depositing at least one of a protein layer and one of a polyphenol layer to thereby form a multi-layered shell structure enveloping an active ingredient; wherein said protein layer is selected such that said shell structure is resistant to degradation under gastric conditions but is degradable by one or more intestinal enzyme.

This deposition step may comprise interposing oppositely charged layers to form the shell structure. The deposition step may comprise layer by layer (LBL) deposition to create the alternating protein/polyphenol layers of the shell structure. The deposition step may be repeated as needed to achieve a desired thickness of the shell or a desired number of shell layers. Advantageously, the method provides a straightforward synthesis of the core-shell composite structure. The disclosed method further allows various combinations of different proteins and/or polyphenols for adjustment of the dissolution/hydrolysis profile. This in turn allows one to fine-tune the rate of delivery of the active ingredient, with potential applications as controlled-release or sustained-release pharmaceutical carriers. This customizable feature further allows one to select with reasonable accuracy the intended site of delivery of the active ingredient, e.g., by using particular proteins hydrolysable by indigenous/site-specific enzymes in the shell structure.

Definitions

The following words and terms used herein shall have the meaning indicated:

The term "active ingredient" as used herein may be interpreted broadly to include a physiologically active compound, including but not limited to, antioxidants, antimicrobials, antiviral, antifungal, antithrombotic agents, anti-inflammatory agents, anticarcinogenic agents, analgesic, immune modulators, regulators of lipid metabolism, amino acids, lipids, peptides, proteins, plant extracts, phytochemicals, saccharides, enzymes, hormones, receptor inhibitors, receptor agonists, and vitamins.

As used herein, the term "gastric condition" refers to a biological or physiological gastric condition or an environment that simulates the same comprising a fluid or aqueous medium having a pH of less than 4.5 and comprising at least one gastric enzyme.

The term "gastric enzyme" is to be interpreted to include an enzyme in the gastric fluid which breaks down macromolecules into smaller molecules that can be absorbed by the human body. The term "gastric enzyme" as used herein may include an enzyme in the gastric fluid that breaks down protein, glycerides, or fatty acids. The term "gastric condition" when used herein in relation to a simulated gastric fluid is to be interpreted in the same manner as defined above.

As used herein, the term "intestinal enzyme" is to be interpreted broadly to include an enzyme found in the intestinal fluid that breaks down macromolecules into smaller molecules that can be absorbed by the human body. This may include enzymes secreted by the small intestine or enzymes secreted by another organ (e.g. pancreas) into the intestinal environment.

The term "polyelectrolyte", as used herein, is to be interpreted to include an oligomeric or a polymeric compound which upon dissolution in a solvent (e.g. water) may be either positively or negatively charged. The term "polyelectrolyte" as used herein may refer to either a polycation or a polyanion. The term "polycation" as used herein refers to an oligomeric or a polymeric compound having more than one positive charges at several sites. The term "polyanion" as used herein refers to a oligomeric or an polymeric compound having more than one negative charges at several sites. Examples of polycations include but are not limited to poly(L-arginine) or "PLA" and poly(L-lysine) or "PLL".

The term "protease" or the term "proteolytic enzyme" may be used interchangeably and refer to proteins or enzymes which break down proteins into polypeptides, polypeptides into peptides, and/or peptides into their amino acid residues.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

Detailed Disclosure of Embodiments

Exemplary, non-limiting or preferred embodiments of the present invention will now be disclosed.

The present disclosure relates to a core-shell composite material comprising: a) a core optionally comprising an active ingredient compound; b) a shell structure comprising at least two alternating layers; the alternating layers being selected from a protein layer or a polyphenol layer; and optionally, c) a polyelectrolyte layer interfacing said core and said shell structure, said polyelectrolyte layer being disposed adjacent to said protein layer or said polyphenol layer, wherein said shell structure is selected to be resistant to degradation under gastric conditions but is degradable by one or more intestinal enzymes.

The core-shell composite material may be a particle, a micro-sized or a nano-sized particle.

The core-shell composite material may exhibit a total thickness of the shell structure of around 5 to 100 nm. The thickness of the shell structure may be substantially uniform. The thickness may be advantageously adjusted according to the residence time of the composite material in the GI tract. In embodiments, the thickness may be selected from 5, 10, 15, 20, 25, 30, 35, 40, 45, 50, 55, 60, 65, 70, 75, 80, 85, 90, 95, 100 nm or the thickness may be provided in a range having an upper and lower limit selected from these values. Each protein layer or polyphenol layer of the shell structure may be independently from 1 to 10 nm thick.

The core-shell composite material may be substantially spherical in shape and has a diameter of about 0.5 μm to about 10 μm. The core-shell composite material may have an average diameter of about 500 nm, 600 nm, 700 nm, 800 nm, 900 nm, 1 μm, 2 μm, 3 μm, 4 μm, 5 μm, 6 μm, 7 μm, 8 μm, 9 μm or 10 μm. The core-shell composite material may comprise substantially monodisperse particles, each having substantially the same average diameter. The core-shell material may also comprise particles having a distribution of average diameters.

The protein layer may be substantially resistant to degradation by gastric digestive enzymes, wherein the degradation-resistant protein may be characterized by having a ratio of amino acid ("aa") residues cleavable by gastric enzymes to total amino acid residues of less than 30%. In embodiments, this ratio may be 30%, 28%, 26%, 24%, 22%, 20%, 18%, 16%, 14%, 12%, 10%, 8%, 6%, 4%, or 2% or less. In embodiments, the protein may be substantially inert to gastric enzymes. In some embodiments, the protein may be one that is not decomposed or hydrolysed by pepsin.

Additionally or alternatively, the protein layer may be further characterized by having a ratio of total cleavable aa residues to total aa residues of more than 35%. Total cleavable AA residues include AA residues cleavable or hydrolysable by both gastric and intestinal enzymes. In some embodiments, this ratio may be 35%, 40%, 45%, 50%, 55%, 60% or more. Advantageously, the protein layer may be one that is less than 30% hydrolyzed when exposed to gastric enzymatic activity but is more than 35% hydrolyzed when exposed to intestinal fluid.

In embodiments, the protein may be one characterized as one having more active sites or amino acid residues which are cleavable by an intestinal enzyme relative to amino acid residues or active sites cleavable by a gastric enzyme, provided that the total fraction of the cleavable active sites or amino acid residues is at least or greater than 35%.

In other embodiments, the protein may comprise any combination of a percentage of gastric-enzyme cleavable active sites as disclosed herein with a percentage of total cleavable active sites as disclosed herein. For instance, the fraction of gastric-enzyme cleavable active sites may be about 30% and the total cleavable sites may be 60% or wherein the fraction of gastric-enzyme cleavable active sites may be about 10% and the total cleavable sites may be about 35%.

The amino acid sequences of proteins can be obtained from GenBank (NCBI US National Center for Biotechnology Information) and the Uniprot Universal (Protein Resource Swiss-Prot/TREMBL/PIR) databases. The determination or prediction of cleavage sites, i.e., amino acid sequences in proteins cleaved by gastrointestinal enzymes (e.g., pepsin for gastric fluid, and trypsin+chymotrypsin for intestinal fluid) can be conducted by means of PeptideCutter (EXPASY, SwissModel) and Uniprot Universal (Protein Resource Swiss-Prot/TREMBL/PIR) programs.

The core-shell composite material may comprise, as an outermost layer of its shell structure, a polyphenol layer. The polyphenol may be branched, hyperbranched or dendritic in structure. The polyphenol may comprise ester linkages, ether linkages, bi-aryl linkages or mixtures thereof.

The polyphenol may be derived from phenolic acids, e.g., benzoic acids, hydroxybenzoic acids or cinnamic acids. The polyphenol may be a dietary polyphenol that is naturally occurring or is synthetic. The polyphenol may be biocompatible. The polyphenol may be selected from, or is a derivative of gallic acid, catechins, epicatechins, proanthocyanidins, anthocyanidins, galloylated catechins, flavonoids, isoflavonoid, neoflavonoids, flavones, or tannins.

In one embodiment, the polyphenol is derived from a mixture of gallic acid esters and proanthocyanidins, wherein the polyphenol comprises at least one or a plurality of galloyl functional groups. In one embodiment, the polyphenol is tannin or tannic acid (TA) or salts and derivatives thereof. Advantageously, the polyphenol having galloyl functional groups or TA may express greater binding affinity or reactivity with proteins such as proteolytic enzymes, relative to polyphenols which are not derived from gallic acid. In one embodiment, the outermost polyphenol layer may be reactive with at least one gastric digestive enzyme to thereby bind a layer of said gastric digestive enzyme into the core-shell particle. This may have the effect of transforming the outermost layer of the core-shell composite particle to a layer composed of the gastric enzyme.

For instance, when provided as the outermost layer of the shell structure, the polyphenol may advantageously bind with a gastric enzyme such as pepsin. This may result in the formation of an outermost pepsin layer, which would further shield the core-shell composite structure and its encapsulated contents from the gastric enzymes. This may enhance the resistance to degradation of the core-shell composite when exposed to gastric conditions.

In one embodiment, the core-shell composite particle may be contacted, partially or completely, with an aqueous medium comprising pepsin prior to being administered to a subject. Doing so may advantageously improve the resistance to degradation when the core-shell particle passes through the stomach.

Optionally, the core-shell composite may comprise a polyelectrolyte layer interposed between the shell structure and the core comprising the active ingredient. The polyelectrolyte layer may provide a seed layer substantially encapsulating the whole of the active ingredient core. The polyelectrolyte layer may be a polycation, or a polyanion selected to bond chemically and/or electrostatically to an adjacent protein layer or an adjacent polyphenol layer. The polyelectrolyte may be biocompatible and non-toxic to a human or animal. The polyelectrolyte may be naturally occurring. The polyelectrolyte may be selected from poly (L-lysine), poly(L-arginine), chitosan, dextran, dextran derivatives, starch, starch derivatives, cellulose or cellulose derivatives, preferably selected from poly(L-lysine) or poly (L-arginine).

The protein of the disclosed core-shell composite may be selected from the group consisting of: alpha-s1-casein, pepsin, bovine serum albumin (BSA), ovalbumin, lysozyme, hemoglobin from bovine blood, chymotrypsin, b-lactoglobulin, trypsin, ubiquitin, lectin, lactoperoxidase, myosin from rabbit muscle, actin, kappa-casein, beta-casein, alpha-lactalbumin, elastin from bovine neck ligament, ferritin and combinations thereof. The protein may be selected to undergo less than 30% degradation under gastric conditions but more than 35% overall degradation when exposed to intestinal fluid. In specific embodiments, the protein is selected from BSA or pepsin.

The gastric conditions may be characterized by about pH 3 or lower, and wherein the core-shell composite is contacted with at least one gastric enzyme e.g., pepsin.

The intestinal fluid may comprise one or more enzymes secreted from the pancreas or the small intestine. The enzymes may be secreted through exocrine glands of the pancreas and directly into the intestines, e.g., chymotrypsin. The enzyme maybe secreted locally by the small intestine, e.g., aminopeptidase. The intestinal enzyme may be selected from the group consisting of: trypsin, chymotrypsin, elastase, enterokinase, carboxypeptidase, aminopeptidase, dipeptidase and mixtures thereof. In one embodiment, the intestinal enzyme is trypsin or chymotrypsin or a mixture thereof.

The compound or active ingredient to be transported may be selected from the group consisting of: a pharmaceutically active compound or salt thereof, food additives, polysaccharides, a hormone, a bioactive, a protein, an enzyme, a peptide, a polypeptide, a prebiotic, a phytochemical (e.g. proanthocyanidin), a probiotic (e.g., such as maltodextrin), a vitamin and mixtures and complexes thereof. In particular embodiments, the compound to be transported by the core-shell composite particles is selected from lactoferrin ("Lf") or bovine colostrum. The transported compound may include enzyme inhibitors e.g., inhibitors of glycoside hydrolase enzymes.

Another embodiment of the present invention relates to a method of preparing a core-shell composite material, the method comprising the steps of: depositing, in alternate manner, at least one of a protein layer and one of a polyphenol layer to thereby form a multi-layered shell structure encapsulating an active ingredient core; wherein said protein layer is selected such that said shell structure is resistant to degradation under gastric conditions but is degradable by one or more intestinal enzyme. In the disclosed method, the polyphenol and the protein may be as described herein.

The depositing step (a) may comprise layer-by-layer deposition. For instance, the method may comprise alternatingly mixing the active ingredient in a protein solution to form a protein layer over said active ingredient, and subsequently mixing the protein-coated active ingredient with a polyphenol solution to form a polyphenol layer over said protein layer. The process may be repeated as needed to form a multi-layered shell structure having a required thickness.

Each protein deposition step or polyphenol deposition step may be independently repeated as needed to obtain a sufficiently thick layer. In one embodiment, more than one mixing step may be undertaken when depositing the protein or polyphenol layers. For instance, a protein layer may be repeatedly deposited to achieve a particular desired thickness before being further encapsulated or enveloped with a polyphenol layer.

The mixing step may be undertaken at ambient conditions. The mixing step may comprise physical agitation, e.g., stirring. Between each deposition step, there may be a washing step to remove residual protein or polyphenol.

The method may comprise depositing protein and polyphenol layers having substantially the same thickness. The method may also comprise depositing protein and polyphenol layers with varying thickness. In one embodiment, the method may comprise depositing protein layers that are substantially thicker than said polyphenol layers, and vice versa.

The active ingredient may be provided on a solid support. For instance, the active ingredient may be adsorbed or absorbed onto a solid support, e.g., $CaCO_3$. The support may be inorganic. The support may also be porous. The solid support may be in the form of particles having micron-sized or nano-sized diameters.

The active ingredient may be optionally encapsulated by a polyelectrolyte prior to deposition with protein or polyphenol. The polyelectrolyte may be one as disclosed herein. The polyelectrolyte may be deposited by contacting the active ingredient (or the solid support comprising the active ingredient) into a polyelectrolyte solution; and precipitating a layer of polyelectrolyte to thereby encapsulate the active ingredient. The polyelectrolyte may be selected from poly (L-lysine), poly(L-arginine), chitosan, dextran, starch, cellulose or derivatives thereof. More than one polyelectrolyte layer may be provided. In one embodiment, the polyelectrolyte is selected from poly(L-lysine) or poly(L-arginine).

The method may further comprises a step of removing the solid support prior to, during or after said deposition step. The removing step may comprise chemically decomposing said solid support. In embodiments, the support material may be retained or left intact after the core-shell composite has been formed. The support material may be reactive with one or more components found in gastric fluid. In embodiments, the support material may react with hydrochloric acid and decompose in the stomach. In other embodiments, the support material may react with acid to form additional barrier layers surrounding the active ingredient.

The method may comprise depositing the protein layer as the innermost layer, e.g., the layer immediately adjacent to the polyelectrolyte layer where provided or the layer immediately adjacent to the active ingredient core where the polyelectrolyte layer is absent. Alternatively, the method may comprise depositing the polyphenol layer as the innermost layer.

In the disclosed method, the protein is preferably one as disclosed herein, e.g., characterized by having a ratio of amino acid residues cleavable by said gastric enzymes to total amino acid residues of less than 30%. The ratio may be less than 30%, 28%, 26%, 24%, 22%, 20%, 18%, 16%, 14%, 12%, 10%, 8%, 6%, 4%, or 2%. Additionally, the protein may be further characterized by having a ratio of total cleavable residues to total amino acid residues of more than 35%.

The protein may be selected from alpha-s1-casein, pepsin, bovine serum albumin (BSA), ovalbumin, lysozyme, hemoglobin from bovine blood, chymotrypsin, b-lactoglobulin, trypsin, ubiquitin, lectin, lactoperoxidase, myosin from rabbit muscle, actin, kappa-casein, beta-casein, alpha-lactalbumin, elastin from bovine neck ligament or ferritin, e.g., BSA or pepsin.

In the disclosed method, the polyphenol may be derived from phenolic acids, e.g., benzoic acids, hydroxybenzoic acids or cinnamic acids. The polyphenol may be a dietary polyphenol that is naturally occurring or is synthetic. The polyphenol may be biocompatible. The polyphenol may be selected from, or is a derivative of gallic acid, catechins, epicatechins, proanthocyanidins, anthocyanidins, galloylated catechins, flavonoids, isoflavonoid, neoflavonoids, flavones, or tannins.

In one embodiment, the polyphenol is derived from a mixture of gallic acid esters and proanthocyanidins, wherein the polyphenol comprises at least one or a plurality of galloyl functional groups. In one embodiment, the polyphenol is tannin or tannic acid (TA) or salts and derivatives thereof.

The active ingredient core may be selected from the group consisting of: a pharmaceutically active compound or salt thereof, food additives, polysaccharides, a hormone, a bioactive, a protein, an enzyme, a peptide, a polypeptide, a prebiotic, a phytochemical (e.g. proanthocyanidin), a probiotic (e.g., such as maltodextrin), a vitamin and mixtures and complexes thereof. In particular embodiments, the active ingredient encapsulated within the core-shell composite particle is selected from lactoferrin or bovine colostrum.

In one embodiment, there is provided the core-shell composite as disclosed herein for use in therapy, e.g., as a pharmaceutically acceptable vehicle for drug delivery.

There is also provided the use of the core-shell composite as disclosed herein in the manufacture of a medicament, wherein said medicament is configured to deliver an active ingredient to the small intestine of a human or animal. The medicament may be formulated for enteric, oral, or intravenous administration. The medicament may further comprise one or more pharmaceutically acceptable excipients.

Advantageously, the core-shell composite may be used as a carrier or a vehicle for a targeted delivery of an active ingredient, such as a protein or an enzyme or a pharmaceutically active compound or salt thereof, wherein the disclosed composite is configured to deliver the active ingredient to the small intestine (including duodenum, jejunum and the ileum), large intestine or colon. This is particularly useful for drugs administered enterically through the GI tract but wherein the drugs are not suitable for or not capable of absorption in the stomach.

BRIEF DESCRIPTION OF DRAWINGS

The accompanying drawings illustrate one or more disclosed embodiments and serves to explain the principles of the disclosed embodiment. It is to be understood, however, that the drawings are designed for purposes of illustration only, and not as a definition of the limits of the invention.

FIG. 1

FIG. 1 contains SEM images of (a) porous $CaCO_3$ microparticles with absorbed Lf, (b) PLL-(BSA-TA)$_4$ shell encapsulating the Lf absorbed $CaCO_3$ microparticles, and (c) PLL-(BSA-TA)$_4$ shell encapsulating the Lf after dissolution of $CaCO_3$ microparticles.

FIG. 2

FIG. 2 is (a) mass resolved 50 µm×50 µm images (C and Fe maps) of positive ions from Lf-loaded PLL-(BSA-TA)$_4$ shells. Brighter colour corresponds to higher intensity of the respective elements while black regions correspond to the absence of the respective elements. (b) Histogram of Fe/C peak intensities ratio showing the distribution of Lf within the individual Lf-loaded PLL-(BSA-TA)$_4$ shells.

FIG. 3

FIG. 3 shows the graphical representations of the assembly of (a) (BSA-TA)$_4$ and (b) (pepsin-TA)$_4$ multilayer films on a flat silicon surface followed by subjecting the films to degradations in the SGF and SIF under continuous agitation at 37° C. The film thickness is measured in situ by ellipsometry.

FIG. 4

FIG. 4 is CLSM images of (a) BSA-FITC encapsulated PLL-(pepsin-TA)$_4$ shells prior to SGF treatment, (b) BSA-FITC encapsulated PLL-(pepsin-TA)$_4$ shells after 1 hour continuous agitation at 37° C. in SGF, and (c) BSA-FITC encapsulated PLL-(pepsin-TA)$_4$ shells after 1 hour continuous agitation at 37° C. in the SGF, followed by 1 hour continuous agitation at 37° C. in the SIF.

FIG. 5

FIG. 5 is SEM images of Lf encapsulated PLL-(BSA-TA)$_4$ shells after (a) 10 min, (b) 30 min, and (c) 60 min continuous agitation in the SGF at 37° C., followed by (d) 60 min continuous agitation in the SIF at 37° C.

FIG. 6

FIG. 6 is graph of the fluorescence intensities ($\lambda_{ex}$=590 nm, $\lambda_{em}$=620 nm) of DQ Red BSA encapsulated in PLL-(BSA-TA)$_4$ (squares), PLL-(BSA-TA)$_8$ (circles), and unencapsulated DQ Red BSA (triangles) upon continuous agitation in the SGF at 37° C. (first 60 min), followed by continuous agitation in the SIF at 37° C. (next 60 min). The inset shows the first 60 min of SGF treatment at a different scale of fluorescence intensities.

FIG. 7

FIG. 7 is SEM images of (a,b) Lf encapsulated PARG-(BSA-TA)$_4$ shells and (c) the absence of observable Lf encapsulated (BSA-TA)$_4$ shells (without a polyelectrolyte anchoring layer) after $CaCO_3$ core dissolution.

FIG. 8

FIG. 8 is SEM image of PLL-(BSA-TA)$_4$ structures obtained after $CaCO_3$ dissolution at pH 1.

EXAMPLES

Non-limiting examples of the invention and a comparative example will be further described in greater detail by reference to specific Examples, which should not be construed as in any way limiting the scope of the invention.

Example 1-1: Preparation of Porous $CaCO_3$ Microparticles with Absorbed Lactoferrin (Lf)

A calcium chloride ($CaCl_2$) solution (720 mL, 1M) is added to aqueous Lf solution (1.8 mL, 1-30 mg/mL). Then, sodium carbonate ($Na_2CO_3$) solution (480 mL, 1M) is injected in one shot under vigorous agitation. Agitation is stopped after 1 min. The resultant dispersion of particles is separated by centrifugation and washing twice using deionized water.

FIG. 1-$a$ shows the Scanning Electron Microscopy (SEM) image of the resultant $CaCO_3$ microparticles with absorbed Lf which are spherical in shape having a particle diameter of between 2 and 4 mm. The rough surface of the spherical particles indicates the presence of large number of pores.

The collected $CaCO_3$ particles with absorbed Lf are dissolved by titration with hydrochloric acid (HCl) (1M) until pH 3. The amount of Lf absorbed into the $CaCO_3$ microparticles is determined by High Performance Liquid Chromatography (HPLC) and Enzyme-Linked Immunosorbent Assay (ELISA) to be 0.8 and 1.0 mg respectively. The calculated concentration of Lf absorbed into the $CaCO_3$ microparticles is about 1.75 wt. %.

Example 1-2: Assembly of Bovine Serium Albumin-Tannic Acid (BSA-TA) Shell on the Surface of $CaCO_3$ Microparticles The $CaCO_3$ microparticles with absorbed Lf from Example 1-1 are immersed into poly(L-lysine) (PLL) solution (2 mL, 2 mg/L) and are shaken continuously for 15 min. Then, the microparticles are collected by centrifugation and the residual PLL is removed by washing twice with deionized water.

Thereafter, the microparticles are re-suspended in aqueous BSA solution (2 mL, 2 mg/mL) (pH 5.8) and are shaken for at least 15 min. The resultant microparticles are collected by centrifugation and the residual BSA is removed by washing twice with deionized water. Subsequently, the microparticles are immersed into aqueous TA solution (2 mL, 2 mg/mL) (pH 3) and are shaken for at least 15 min. The resultant microparticles are collected by centrifugation and the residual TA is removed by washing twice with deionized water. This procedure is repeated until a total of four BSA-TA bilayers are deposited on the microparticles.

FIG. 1-$b$ shows the SEM image of the resultant PLL-(BSA-TA)$_4$ shell deposited on the surface of the microparticles with absorbed Lf having smoother surface compared to the $CaCO_3$ of Example 1-1 which is indicative of successful shell formation.

Example 1-3: $CaCO_3$ Core Dissolution and Formation of BSA-TA Shell with Encapsulated Lf The microparticles of Example 1-2 are collected by centrifugation and re-dispersed in deionized water (1 mL).

Then, HCl solution (1M) is added drop-wise to the dispersion until the about pH 3. The resultant shells with encapsulated Lf are collected by centrifugation and washing twice with deionized water. FIG. 1-c shows the SEM image of the PLL-(BSA-TA)$_4$ shells with the encapsulated Lf wherein the $CaCO_3$ cores are completely dissolved.

The amount of encapsulated Lf in the individual shell and the distribution of encapsulated Lf among the shells in a batch are evaluated by Secondary Ion mass Spectrometry (SIMS). A suspension of the Lf encapsulated in the PLL-(BSA-TA)$_4$ shells is deposited on a copper substrate, is allowed to dry in air at ambient temperature, and is put under vacuum. After surface contamination is removed from the shell with $Ar^+$ beam, a 50 µm×50 µm area is scanned by the analysis beam of $Bi^+$ ions and a mass spectrum is obtained from each pixel of the scan. The peaks corresponding to C and Fe positive ions are identified in the mass spectra, their intensities are integrated and plotted versus the primary ion beam position. FIG. 2-a shows typical images of PLL-(BSA-TA)$_4$ shells with encapsulated Lf, where the image of Fe correlates with that of C. The bright spots show the location of the shell on the copper support since the C and Fe ions originate from the enzyme. The ions in the surrounding area have low intensity.

The amount of Lf encapsulated by the PLL-(BSA-TA)$_4$ shell is determined by calculating the ratio of the Fe to C peak intensities for each individual shell. FIG. 2-b shows the distribution of the amount of Lf encapsulated by the PLL-(BSA-TA)$_4$ shells for a batch of Lf encapsulated shells. The Fe/C peak intensities ratio in the range of 0.2 to 0.9 with an average value of 0.5±0.2 is observed.

Example 2: Protein-Polyphenol Shells in Simulated Gastric and Intestinal Fluids Simulated gastric fluid (SGF) is prepared by mixing sodium chloride (NaCl) solution (4 mL, 150 mM) (adjusted to pH 3 using HCl) with pepsin solution (1 mL, 7.1 mg/mL pepsin, 150 mM NaCl).

Simulated instentinal fluid (SIF) is prepared by mixing the SGF with bile salts solution (1 mL, 120 mM bile salts, 0.1M sodium bicarbonate ($NaHCO_3$)) at pH 7.0 and pancreatin solution (1 mL, 1800 USP U/mL pancreatin, 0.1M $NaHCO_3$) at pH 7.0.

The process of pepsin-TA or BSA-TA multilayer films assembly on a flat surface of a silicon substrate followed by films degradations in SGF and SIF under continuous flow at 37° C. are studied by precision ellipsometry. FIG. 3 shows the increase in film thickness from 0 to 16±2.5 nm and 15±3.9 nm upon assembly of four BSA-TA and pepsin-TA bilayers respectively. In the case of the BSA-TA multilayer shell, the thickness increases even further to 18.2±1.2 nm after 60 min treatment in the SGF. This could be due to absorption of pepsin by the terminal TA layer and its incorporation into the film. Evidently, this is not the case for pepsin-terminated (pepsin-TA) multilayer. Advantageously, the BSA-TA and pepsin-TA films thickness decreases dramatically to 9.5±2.0 and 8.3±3.1 nm respectively after 60 min treatment in the SIF, which indicates the degradation of the films in the small intestine.

A batch of BSA-fluorescein isothiocyanate conjugate (BSA-FITC) encapsulated in the PLL-(pepsin-TA)$_4$ shells is prepared and treated with SGF and SIF under continuous agitation at 37° C. PLL was used as an anchoring layer in this example. Samples are collected before, and after 60 min of treatment in SGF, and after a further 60 min treatment in SIF. Digestion is stopped by pH increase to 7.0 with sodium hydroxide (NaOH) and adding one tablet of phenylmethylsulfonyl fluoride (PMSF). Each sample is centrifuged and washed three times with deionized water. FIG. 4-a shows the Confocal Laser Scanning Microscopy (CLSM) image of well-dispersed BSA-FITC encapsulated in the PLL-(pepsin-TA)$_4$ shells prior to SGF and SIF treatment. FIG. 4-b demonstrates that the BSA-FITC in the encapsulated PLL-(pepsin-TA)$_4$ shells remain stable after 60 min treatment in SGF, with no observable change in sizes or aggregation. FIG. 4-c shows that the BSA-FITC in the encapsulated PLL-(pepsin-TA)$_4$ shells are completely degraded after 60 min treatment in SIF, resulting in the release of fluorescent BSA into the surrounding solution.

A batch of Lf encapsulated PLL-(BSA-TA)$_4$ shells is prepared and treated with SGF and SIF under continuous agitation at 37° C. Samples are collected before, and after 60 min of treatment in SGF, and after a further 60 min treatment in SIF. Digestion is stopped by pH increase to 7.0 with NaOH and adding one tablet of PMSF. Each sample is centrifuged, washed three times with deionized water and freeze-dried. Table 1 presents the weight of the Lf encapsulated PLL-(BSA-TA)$_4$ shells before and after SGF and SIF treatments. The corresponding weight loss after SGF and SIF treatments are calculated to be about 2.2% and 99.1% respectively.

TABLE 1

|   | Capsules, mg | Capsules after stomach, mg | Weight loss, % | Mean weight loss, % | Capsules after intestinal, mg | Weight loss, % | Mean weight loss, % |
|---|---|---|---|---|---|---|---|
| 1 | 1.090 | 1.050 | 3.7 | 2.2 ± 1 | 0.010 | 99.1 | 99.1 ± 0.2 |
| 2 | 1.010 | 1.000 | 1.0 |  | 0.009 | 99.1 |  |
| 3 | 0.980 | 0.960 | 2.0 |  | 0.006 | 99.4 |  |
| 4 | 1.130 | 1.100 | 2.6 |  | 0.011 | 99.0 |  |
| 5 | 1.070 | 1.050 | 1.9 |  | 0.013 | 98.8 |  |

Another batch of Lf encapsulated PLL-(BSA-TA)$_4$ shells is prepared and treated with SGF and SIF under continuous agitation at 37° C. Samples are collected after 10 min, 30 min, and 60 min in the SGF, and after 60 min in the SIF. Digestion is stopped by pH increase to 7.0 with NaOH and adding one tablet of PMSF. Each sample is centrifuged and washed three times with deionized water. FIG. 5 shows the SEM images of the PLL-(BSA-TA)$_4$ shells with encapsulated Lf after treatment in the SGF and SIF. The change in the PLL-(BSA-TA)$_4$ shells after an hour treatment in the SGF appears to be minimal and insignificant. In contrast, the number of observable PLL-(BSA-TA)$_4$ shells remaining in the sample after an hour of treatment in SIF decreases significantly. Only a few shells are visible by the SEM.

Example 3: Protection Efficiency of Encapsulated Proteins in SGF Followed by their Release in the SIF A blank sample with unprotected DQ Red BSA proteins is prepared according to the method described in Examples 1-1 and 1-3. Samples of DQ Red BSA proteins encapsulated in PLL-(BSA-TA)$_4$ and PLL-(BSA-TA)$_8$ shells are prepared according to the method described in Examples 1-1 to 1-3.

DQ Red BSA proteins are derivatives of BSA heavily labelled with BODIPY dyes. Hydrolysis of DQ Red BSA by proteases results in single, dye-labeled peptides which are brightly fluorescent products.

The blank sample and the samples of PLL-(BSA-TA)$_4$ and PLL-(BSA-TA)$_8$ shells encapsulating the DQ Red BSA are subjected to treatment in the SGF and SIF under continuous agitation at 37° C. Samples are collected after 10 min, 30 min, and 60 min in the SGF, and after 10 min, 30 min and 60 min in the SIF. The fluorescence spectra of the collected samples are recorded and the fluorescence intensities of emission band at $\lambda=620$ nm for all samples are shown in FIG. 6. Fluorescence intensities of encapsulated DQ Red BSA are very low during 60 min of treatment time in SGF, but increases drastically upon introduction of the samples into the SIF. For unprotected DQ Red BSA, fluorescence intensity increases upon treatment in SGF followed by even more pronounced increase upon treatment in SIF.

The protective efficiency (P.E.) provided by the encapsulation is defined as follow:

$$P.E.=(1-I_x/I_0)*100\%,$$

where $I_x$ is fluorescence intensity of the protein encapsulated in PLL-(BSA-TA)$_4$ or PLL-(BSA-TA)$_8$ shell and $I_0$ is fluorescence intensity of unprotected protein in the same point of treatment time.

The P.E. provided by the PLL-(BSA-TA)$_4$ and PLL-(BSA-TA)$_8$ shells after 60 min of treatment in SGF are 76±6% and 85±2% respectively.

Comparative Example 1

Poly(L-arginine) (PARG) is used as the anchoring instead of PLL. Lf encapsulated in PARG-(BSA-TA)$_4$ shells are prepared according to the method described in Examples 1-1 to 1-3. In addition, Lf encapsulated (BSA-TA)$_4$ shells without an anchoring layer is prepared by the method described in Examples 1-1 to 1-3 except that the step of immersing the microparticles in PLL solution is skipped. FIG. 7 shows the SEM images of these samples after CaCO$_3$ dissolution. PARG-(BSA-TA)$_4$ shells are of about the same size, shape and integrity as PLL-(BSA-TA)$_4$ shells shown in FIG. 1. On the contrary, no shells are found in the sample without an anchoring layer of polyelectrolyte.

Comparative Example 2

FIG. 8 shows the SEM image of the sample as in FIG. 1-c (described in Example 1-3), but dissolved in HCl at pH~1. Collapsed shell structure is observed and no stable shells are found in this sample. Thus, although (BSA-TA) shells are stable at pH level of the gastric fluid of healthy people, they may degrade in gastric fluid of people with certain diseases that causes higher gastric acidity.

INDUSTRIAL APPLICABILITY

The potential industrial applications of the disclosed core-shell composite particle or material are self-evident. Most particularly, the disclosed core-shell composite material will be advantageously useful in transporting compounds intended for reaction or absorption in the small intestine (including the jejunum, duodenum or ileum), especially where these compounds may be pH sensitive or may be potentially degraded by pepsin or other stomach enzymes without the protection of the core-shell structure.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A core-shell composite material comprising:
   a. a core optionally comprising an active ingredient compound;
   b. a shell structure comprising at least two layers; said at least two layers being alternately a protein layer or a polyphenol layer; and
   c. a polyelectrolyte layer interposed between said core and said shell structure,
   wherein said shell structure is selected to be resistant to degradation under gastric conditions but is degradable by one or more intestinal enzymes,
   wherein said protein layer consists of a protein selected from alpha-s1-casein, pepsin, ovalbumin, lysozyme, hemoglobin from bovine blood, chymotrypsin, b-lactoglobulin, trypsin, ubiquitin, lectin, lactoperoxidase, myosin from rabbit muscle, actin, kappa-casein, beta-casein, alpha-lactalbumin, elastin from bovine neck ligament or ferritin,
   wherein said polyelectrolyte layer comprises a polyelectrolyte selected from poly(L-lysine), poly(L-arginine), dextran, starch, cellulose or derivatives thereof,
   wherein the outermost layer of said shell structure is a polyphenol layer,
   wherein said outermost polyphenol layer is characterized by being reactive with at least one gastric digestive enzyme to thereby bind a layer of said gastric digestive enzyme thereon or
   wherein each polyphenol layer is independently selected from, or is a derivative of, gallic acid, catechins, epicatechins, anthocyanidins, galloylated catechins, flavonoids, isoflavonoid, neoflavonoids, flavones, or tannins or
   wherein the outermost polyphenol layer is tannin, tannic acid or a derivative thereof and
   wherein the total thickness of the shell structure is 5 to 100 nm or wherein said core-shell composite material is spherical in shape and has a diameter of about 0.5 to about 10 μm.

2. The core-shell composite material of claim 1, wherein said protein layer is resistant to proteolytic degradation by gastric digestive enzymes, characterized by having a ratio of residues cleavable by said gastric enzymes to total amino acid residues of less than 30% or wherein said gastric digestive enzyme is pepsin.

3. The core-shell composite material of claim 1, wherein said protein layer is further characterized by having a ratio of total cleavable residues to total amino acid residues of more than 35%.

4. The c re-shell composite material of claim 1, wherein said active ingredient is selected from the group consisting of: a pharmaceutically active compound or salt thereof, food additives, polysaccharides, a hormone, a bioactive, a protein, an enzyme, a peptide, a polypeptide, a prebiotic, a phytochemical, a probiotic, a vitamin and mixtures and complexes thereof.

5. The core-shell composite material of claim 1, wherein said gastric conditions are characterized by about pH 3 and the presence of at least one gastric enzyme.

6. The core-shell composite material of claim 1, wherein said one or more intestinal enzymes is one or more enzymes secreted from the pancreas or the small intestine selected from the group consisting of: trypsin, chymotrypsin, elastase, enterokinase, carboxypeptidase, aminopeptidase, dipeptidase and mixtures thereof.

7. A method of preparing a core-shell composite material comprising:
(a) depositing, in alternate manner, at least one protein layer and at least one polyphenol layer to thereby form a shell structure enveloping an encapsulated active ingredient;
wherein said at least one protein layer consists of a protein selected from alpha-s1-casein, pepsin, ovalbumin, lysozyme, hemoglobin from bovine blood, chymotrypsin, b-lactoglobulin, trypsin, ubiquitin, lectin, lactoperoxidase, myosin from rabbit muscle, actin, kappa-casein, beta-casein, alpha-lactalbumin, elastin from bovine neck ligament or ferritin,
wherein said at least one protein layer is selected such that said shell structure is resistant to degradation under gastric conditions but is degradable by one or more intestinal enzymes, wherein said active ingredient is encapsulated by a polyelectrolyte selected from poly (L-lysine), poly(L-arginine), dextran, starch, cellulose or derivatives thereof prior to said deposition and wherein the depositing further comprises depositing the polyphenol layer as the outermost layer,
wherein said outermost polyphenol layer is characterized by being reactive with at least one gastric digestive enzyme to thereby bind a layer of said gastric digestive enzyme thereon or
wherein each polyphenol layer is independently selected from, or is a derivative of, gallic acid, catechins, epicatechins, anthocyanidins, galloylated catechins, flavonoids, isoflavonoid, neoflavonoids, flavones, or tannins or
wherein the outermost polyphenol layer is tannin, tannic acid or a derivative thereof and
wherein the total thickness of the shell structure is 5 to 100 nm or wherein said core-shell composite material is spherical in shape and has a diameter of about 0.5 to about 10 µm.

8. The method of claim 7, wherein said active ingredient is absorbed on a solid support comprising a porous structure.

9. The method of claim 5, wherein said at least one protein layer is resistant to proteolytic degradation by gastric digestive enzymes, characterized by having a ratio of residues cleavable by said gastric enzymes to total amino acid residues of less than 30%.

10. The method of claim 5, wherein said protein layer is characterized by having a ratio of total cleavable residues to total amino acid residues of more than 35%.

11. The method of claim 8, wherein the method further comprises removing said solid support prior to, during or after said deposition or
wherein said removing comprises chemically decomposing said solid support.

12. The method of claim 7, wherein the depositing (a) is a layer-by-layer deposition, comprising alternatingly mixing the active ingredient in a protein solution to form said at least one protein layer and subsequently mixing in a polyphenol solution to form a polyphenol layer over said at least one protein layer, to thereby form said shell structure or
wherein the depositing comprises depositing the at least one protein layer adjacent to said polyelectrolyte layer
wherein the depositing comprises depositing the at least one polyphenol layer adjacent to said polyelectrolyte layer.

13. A method of delivering an active ingredient to a desired location of a human or animal subject comprising administering a core-shell composite material to said subject, wherein said core-shell composite material encapsulates said active ingredient, wherein said core-shell composite material comprises:
a. a core comprising the active ingredient;
b. a shell structure comprising at least two layers; said at least two layers being alternately a protein layer or a polyphenol layer; and
c. a polyelectrolyte layer interfacing said core and said shell structure, said polyelectrolyte layer being disposed adjacent to said protein layer or said polyphenol layer, wherein said shell structure is selected to be resistant to degradation under gastric conditions but is degradable by one or more intestinal enzymes,
wherein said protein layer consists of a protein selected from alpha-s1-casein, pepsin, ovalbumin, lysozyme, hemoglobin from bovine blood, chymotrypsin, b-lactoglobulin, trypsin, ubiquitin, lectin, lactoperoxidase, myosin from rabbit muscle, actin, kappa-casein, beta-casein, alpha-lactalbumin, elastin from bovine neck ligament or ferritin,
wherein said polyelectrolyte layer comprises a polyelectrolyte selected from poly(L-lysine), poly(L-arginine), dextran, starch, cellulose or derivatives thereof,
wherein the outermost layer of said shell structure is a polyphenol layer,
wherein said outermost polyphenol layer is characterized by being reactive with at least one gastric digestive enzyme to thereby bind a layer of said gastric digestive enzyme thereon or
wherein each polyphenol layer is independently selected from, or is a derivative of, gallic acid, catechins, epicatechins, anthocyanidins, galloylated catechins, flavonoids, isoflavonoid, neoflavonoids, flavones, or tannins or
wherein the outermost polyphenol layer is tannin, tannic acid or a derivative thereof and
wherein the total thickness of the shell structure is 5 to 100 nm or wherein said core-shell composite material is spherical in shape and has a diameter of about 0.5 to about 10 µm.

* * * * *

UNITED STATES PATENT AND TRADEMARK OFFICE
CERTIFICATE OF CORRECTION

PATENT NO. : 11,285,114 B2
APPLICATION NO. : 15/771399
DATED : March 29, 2022
INVENTOR(S) : Harjinder Singh et al.

Page 1 of 1

It is certified that error appears in the above-identified patent and that said Letters Patent is hereby corrected as shown below:

In the Claims

| Column | Line(s) | |
|---|---|---|
| 14 | 64 | Claim 4 Delete "c re-shell" and insert --core-shell-- |

Signed and Sealed this
Twenty-seventh Day of June, 2023

Katherine Kelly Vidal
*Director of the United States Patent and Trademark Office*